United States Patent [19]
Darling et al.

[11] Patent Number: 5,698,978
[45] Date of Patent: Dec. 16, 1997

[54] SYSTEM AND METHOD FOR MEASURING ELECTROMAGNETIC RADIATION ABSORPTION

[75] Inventors: Phillip H. Darling, Buena Park; Hoai X. Le, Fountain Valley; Thai Le Khac, Paramount, all of Calif.

[73] Assignee: Northrop Grumman Corporation, Los Angeles, Calif.

[21] Appl. No.: 441,134

[22] Filed: May 15, 1995

[51] Int. Cl.$^6$ .................................................. G01R 33/12
[52] U.S. Cl. .......................... 324/238; 324/240; 324/243; 324/642
[58] Field of Search ........................ 324/228, 233, 324/234, 235, 236, 237, 239, 240, 642

[56] References Cited

U.S. PATENT DOCUMENTS

| | | | |
|---|---|---|---|
| 4,528,506 | 7/1985 | Davis | 324/237 |
| 4,755,753 | 7/1988 | Chern | 324/237 |
| 5,028,100 | 7/1991 | Valleau | 324/238 |
| 5,053,705 | 10/1991 | Herko | 324/240 |
| 5,086,274 | 2/1992 | Gobin | 324/242 |
| 5,363,040 | 11/1994 | Horn | 324/238 |

*Primary Examiner*—Ernest F. Karlsen
*Assistant Examiner*—Jose M. Solis
*Attorney, Agent, or Firm*—Terry J. Anderson; Karl J. Hoch, Jr.

[57] ABSTRACT

A portable measuring device for measuring electromagnetic radiation reflection. The device has a holder, a transceiver, and a display. The transceiver is movably mounted to the holder. The holder can be moved to several locations on a member being tested. The transceiver is moved up and down on the holder through the peaks and valleys of the reflected electromagnetic wave, in and out of phase, passing through and detecting the maximum reflected energy point. A system can be provided that uses the measurement at a predetermined frequency in comparing the measured property to a characteristic curve of the property for the material of the member being tested. The system can be used to plot a three-dimensional graph of surface reflection of the electromagnetic energy.

20 Claims, 6 Drawing Sheets

FREQUENCY (GHz)

SYSTEM AND METHOD FOR MEASURING ELECTROMAGNETIC RADIATION ABSORPTION

CROSS-REFERENCE TO RELATED APPLICATIONS

This is a continuation-in-part of U.S. patent application Ser. No. 08/388,761, filed Feb. 15, 1995, now U.S. Pat. No. 5,574,379 which is a continuation of U.S. Pat. application Ser. No. 07/992,238, filed Dec. 17, 1992, now U.S. Pat. No. 5,393,557.

BACKGROUND OF THE INVENTION

1. Field of the Invention

The present invention relates to a system and method for measuring electromagnetic energy absorption and/or reflection.

2. Prior Art

U.S. Pat. Nos. 5,141,595 and 5,268,062 (Darling, Jr.) disclose a method and apparatus for coating of refractory substrates with a highly uniform layer of graphite or other material. Electrical pick-ups are used with an electronic control and transport motor for physically altering substrate transport velocity, or other parameters, to adjust the coated substrate's properties.

U.S. Pat. No. 4,408,156 (Veys) discloses the use of microwave radiation to detect thin conductive fibers placed on a sheet article of non-conductive material for identification purposes. The system computes the difference between transmitted, and reflected radiation. U.S. Pat. Nos. 4,500,835 (Heikkila) and 4,607,212 (Jakkula) disclose the use of microwave radiation for detecting grain direction and knots in lumber. U.S. Pat. No. 3,818,335 (Stungis et al) discloses use of probes to monitor and detect the applied amounts of conductive material on a moving non-conductive web, after moving. U.S. Pat. No. 2,940,040 (Rosenthal) discloses the measurement of direct current resistivity of plastic materials for quality control purposes. U.S. Pat. No. 5,012,248 (Munro et al.) discloses the measurement of the thickness of a radar absorbing coating by receiving reflected radio frequency energy from the coating through a dielectric impedance matching element which is physically placed against the coating.

"Nondestructive Microwave Scanning Measurements for Material property Evaluation," by P. R. Wims and D. D. palmer, *Review of Progress in Quantitative Nondestructive Evaluation*, vol. 10A , plenum press, New York, 1991, describes a system for measuring properties of radar absorbing material by illuminating small volumes of a test sample with microwave energy while the specimen is maneuvered between two antennas by an automated translation stage.

SUMMARY OF THE INVENTION

In accordance with one method of the present invention, a method of testing an electromagnetic property of a member is provided comprising steps of moving a transceiver towards and away from a portion of the member; and generating an output signal from the transceiver representative of received reflected electromagnetic energy. The transceiver both transmits electromagnetic energy towards the portion of the member being tested and receives reflected electromagnetic energy from the portion as the transceiver is moved towards and away from the portion.

In accordance with one embodiment of the present invention a system for measuring an electromagnetic property of a member is provided. The system comprises a portable scan device and a portable display. The portable scan device has an electromagnetic energy transceiver. The portable display is operably connected to the scan device.

In accordance with another method of the present invention a method of testing an electromagnetic property of a member is provided comprising steps of measuring the electromagnetic property of the member at a first predetermined frequency and comparing the measured property to a characteristic curve of the property for materials of which the member is composed.

BRIEF DESCRIPTION OF THE DRAWINGS

The foregoing aspects and other features of the invention are explained in the following description, taken in connection with the accompanying drawings, wherein.

DETAILED DESCRIPTION OF THE INVENTION

Figure 1:
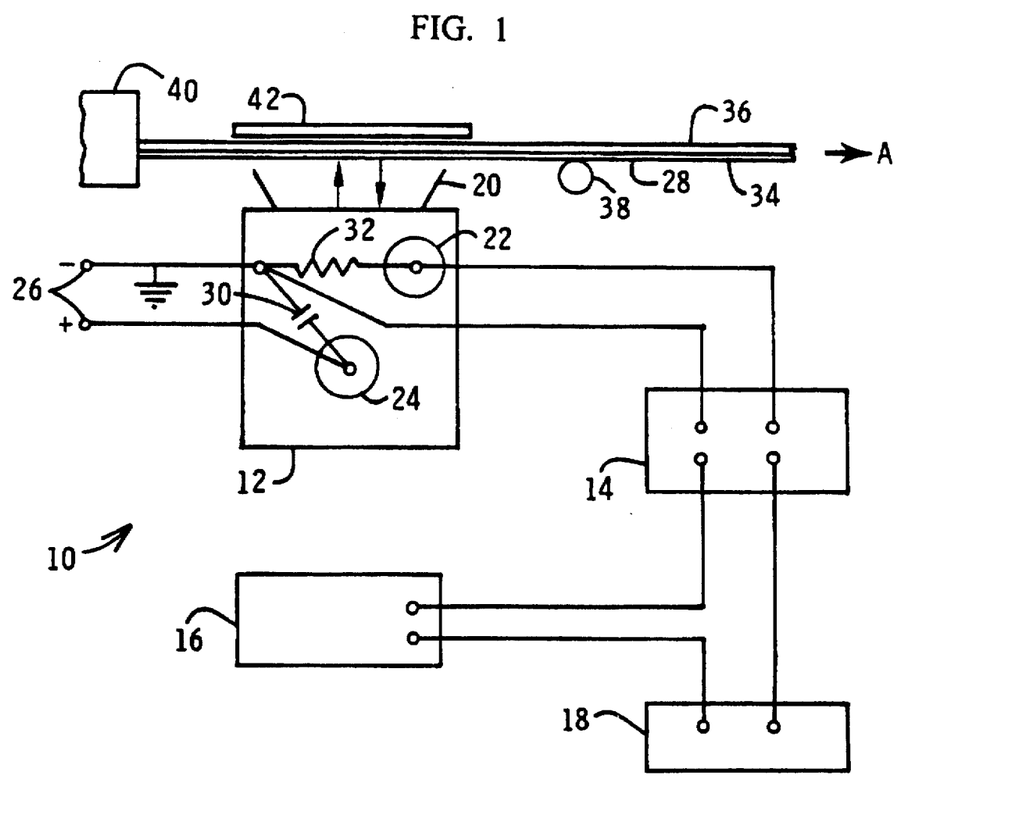
FIG. 1 is a schematic diagram of a system for measuring electromagnetic properties of a member during manufacturing.

FIG. 1 is a schematic diagram of a system 10 used to measure electrical resistivity of a member incorporating features of the present invention. Although the present invention will be described with reference to the embodiments shown in the drawings, it should be understood that the present invention can be embodied in various different forms of alternate embodiment. In addition, any suitable size, shape or type of members, elements or materials could be used as further understood below.

The system 10 generally comprises a transceiver 12, a linearizing amplifier 14, a readout 16, and a controller 18. The transceiver 12 generally comprises an antenna 20, a mixer 22, and an oscillator 24. In a preferred embodiment, the transceiver 12 is an electromagnetic energy transmit and receive unit. The transceiver 12 is preferably a microwave transmit and receive unit such as Type GOS2580 Motion Detector Module manufactured by Alpha Industries, Inc. which can transmit microwave energy at a frequency of about 10.525 GHz. The transceiver 12 operates with an 8 volt DC input at input terminals 26.

The antenna 20 is preferably a horn antenna that can both transmit a nearly parallel unguided beam of microwaves at a member 28 and receive microwaves reflected by the member 28 back to the antenna. The waves entering the antenna as reflected energy produce a DC-voltage across the load resistance. This voltage is representative of the energy reflected. The mixer 22 is preferably a Schottky barrier diode and the oscillator 24 is preferably a Gunn diode that acts as an emitter and local oscillator. The transceiver is supplied with a capacitor 30 fitted between the Gunn bias terminal and ground to suppress bias circuit oscillations. The mixer output terminal is fitted with a load resistor 32, such as a 12K resistor.

Figure 2:
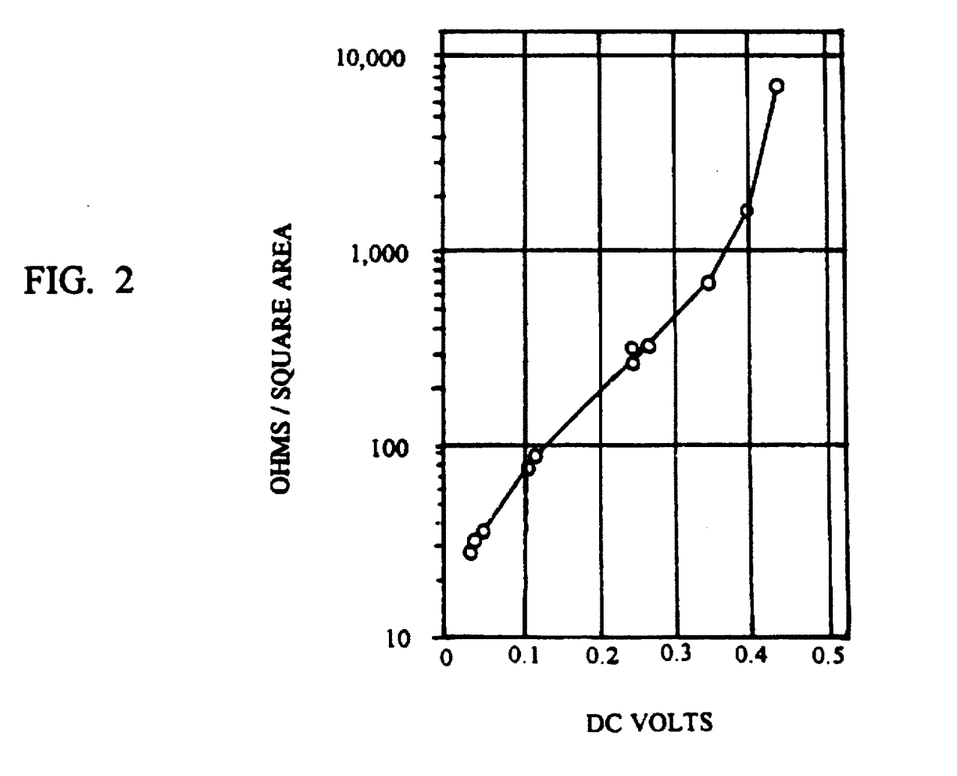
FIG. 2 is a graph of sample test results of the system shown in FIG. 1.

The DC voltage component of the mixer, output to amplifier 14 for the preferred embodiment described above, is shown in FIG. 2. The output is proportional to the electrical resistance of the member 28 at the antenna 20. FIG. 2 shows the output of the transceiver 12, measured in DC volts, plotted relative to the resistivity of the area of member 28 at the antenna 20 as further understood below. In actuality, the area used in the resistivity calculation is the volume of the member 28 at the antenna 20, but is described herein as the simplified term of area due to the relatively thin thickness of the member 28.

In order to insure accurate and uniform measurements of reflected microwave energy, the system 10 includes a backing plate 42 located opposite the antenna 20. The backing plate 42 is provided to insure that the member 28 is in a restrained plane at the area of the antenna 20 while being tested. However, any suitable type of restraining system could be provided. In addition, the backing plate 42 also provides the function of at least partially constraining the member 28 at a predetermined spacing from the antenna 20. However, any suitable type of spacing system could be provided.

The DC voltage component of the mixer output is sent to the linearizing amplifier 14. In a preferred embodiment, a linearizing DC transmitter, such as AP4155 manufactured by Action Instruments Inc. of San Diego, Calif., is used. The linearizing amplifier 14 has an input amplifier, in a series of twelve gain stages, and an output amplifier. The DC signal is fed to the input amplifier which drives the series of twelve gain stages. The gain stages are activated in turn at DC input levels predetermined at the factory for best 12-segment linearization; the segments are more closely grouped at the most non-linear portions of the input curve. Each stage adds to or subtracts from the gain of the preceding stage as necessary to correct the input non-linearity. The linearization stage allows adjustment of zero, and drives an output buffer stage which allows adjustment of span. The amplifier 14 produces a current output (e.g. 4–20 mA) that is a constant-current source controlled by the buffer stage. For a DC input of 49 mv to 450 mv, the output is preferably between about 4 mA to about 20 mA.

The current output from the linearizing amplifier 14 is directed to the readout 16 and the drive control 18. The readout 16 is preferably a digital readout, such as the VISIPAK V500 line of digital process indicators manufactured by Action Instruments, Inc. of San Diego, Calif., to display a readout in ohms per square area at antenna 20. The controller 18 is part of a coating system adapted to apply a high temperature coating 34 to a sheet material 36 that constitutes the member 28. Any suitable drive, such as drive rollers 38, can be used to help move the member 28 in the direction illustrated by arrow A out of the coating applicator 40. The controller 18 is adapted to control the speed of the drive and thereby control the amount of coating being applied to a length of the sheet material 36.

In a preferred method of the present invention, the sheet material or substrate 36 is made of a woven-type yarn, such as NEXTEL 312 fiber having 62% aluminum oxide ($Al_2O_3$), 14% boron oxide ($B_2O_3$), and 25% silicon dioxide ($SiO_2$) by weight. The fibers are woven into a fabric of 300 denier, 5 harness satin weave, 60×60 yarns/inch. Of course, any suitable substrate could be used.

The coating applicator 40 is substantially the same as the system described in U.S. Pat. Nos. 5,141,595 and 5,268,062 which are hereby incorporated by reference. The system 40 is used to apply the electrically conductive superstrate or graphite coating 34 to the substrate 36. The faster the speed of the substrate 36 through the system 40, the thinner the layer of superstrate 34. The thinner the layer of superstrate 34, the higher the resistivity of the member 28. Thus, the faster the speed of the substrate 36 through the system 40, the higher the resistivity of the member 28. Conversely, the slower the speed of the substrate 36 through the system 40, the thicker the layer of superstrate 34 and the lower the resistivity of the member 28. The controller 18, by controlling the speed of the substrate 36 through the system 40, can thus control the final resistivity of the member 28. Of course, in an alternate embodiment of the present invention, rather than the controller 18 being connected to the drive, the controller 18 could be connected to a valve that regulates precursor gas flow, a thermostat that regulates oven temperature, or a combination of these parameters.

The value of a given property of the coated substrate depends upon the physico-chemical make-up of the superstrate coating. Altering the conditions within the chemical vapor deposition zone by adjusting a parameter, such as substrate transport velocity, flow rate or oven temperature, results in a modification of the properties of the coated substrate. Thus, the described feedback mechanism provides a means for maintaining the value of superstrate properties within desirable tolerances.

At initial start of manufacture of the member 28, the speed of the substrate drive is set at a predetermined value. The system 10 will operate during this initial start. However, the controller 18 is preferably programmed to ignore signals from the system 10 until the resistivity measurements reach a predetermined range of resistivity measurements. preferably, the drive also has a manual control that can be adjusted by an operator viewing readout 16 to bring the speed up or down until the predetermined range is met. When the predetermined range is met, the controller 18 can then automatically take control of the substrate drive to continuously monitor, and increase or decrease the speed of the substrate 36 through the system 40, to maintain the value of superstrate properties within preprogrammed desirable tolerances. The system 10 may also include a suitable marker to mark the member 28 at the point where it reaches desirable tolerances. Thus, the leading portion of the member 28 before the marker's mark can be removed and discarded for quality control purposes.

Unlike the electrical pick-ups disclosed in U.S. Pat. Nos. 5,141,595 and 5,268,062 and the testing device disclosed in U.S. Pat. No. 5,012,248, the system shown in FIG. 1 is adapted to test resistivity of the member 28 without physically contacting the member 28. The system 10 is able to measure resistivity over an area of about 1 to 2 square inches at a distance of about ½ inch away from the member 28. Of course, the antenna 20 could be suitably sized, shaped, and positioned to provide any suitable testing parameters. This can be important in testing members such as conductive fabric or sheet material because such a relatively large test area can encompass a large enough number of yarns that individual variations and gaps between yarns of the fabric are averaged out. Thus, the measurements are substantially insensitive to yarn variations.

The present invention can also be used to test magnetic susceptibility in non-conductive materials. This is due to the fact that the output from the transceiver 12 is also affected by the magnetic susceptibility of a material being tested. Unlike the system described in U.S. Pat. No. 4,408,156, the system shown in FIG. 1 is much simpler. The system 10 merely measures reflected radiation which is then linearized and calibrated in surface resistance units. U.S. Pat. No. 4,408,156 computes the differences among transmitted, absorbed, and reflected energy and needs two sensors located on both sides of the sheet article. In addition, unlike U.S. Pat. No. 4,408,156, the system 10 is used in an active manufacturing quality control system and not merely an identification system. In a preferred embodiment, the microwave radiation from the transceiver is polarized. Conductive fabric yarns that are perpendicular to the electric field E are not significantly detected. This would also be the case for magnetically susceptible yarns relative to the magnetic field H which is perpendicular to the electric field E.

Some military air combat vehicles require magnetically susceptible or electrically conductive low observable coatings to delay or avoid radar detection. Low observable coatings are usually applied as sprayed slurries of magnetic or conductive particles in a polymetric or ceramic matrix. The radar absorption performance of such coatings cannot be verified until after they are cured. The system 10 shown in FIG. 1 can be used to control initial application of the sprayed and cured slurries. The system 50 shown in FIG. 3 can be used outside of the manufacturing facility for identification and repair of damaged surfaces.

Figure 3:
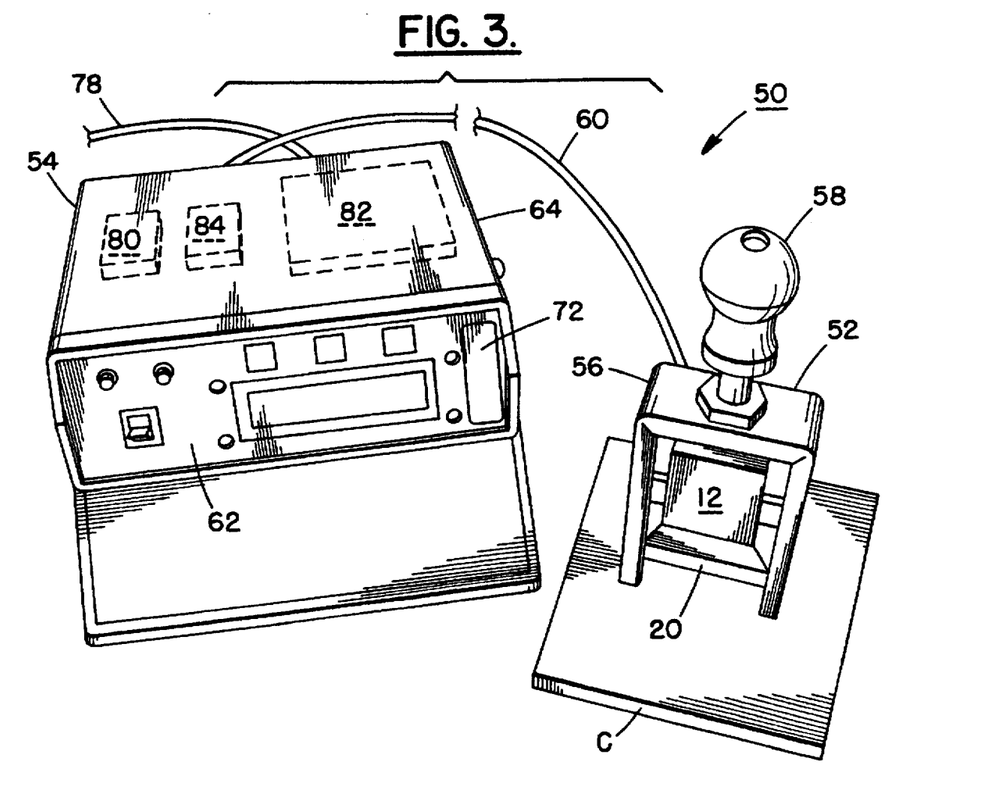
FIG. 3 is a perspective view of a portable system for measuring an electromagnetic property of a member.
Figure 3A:
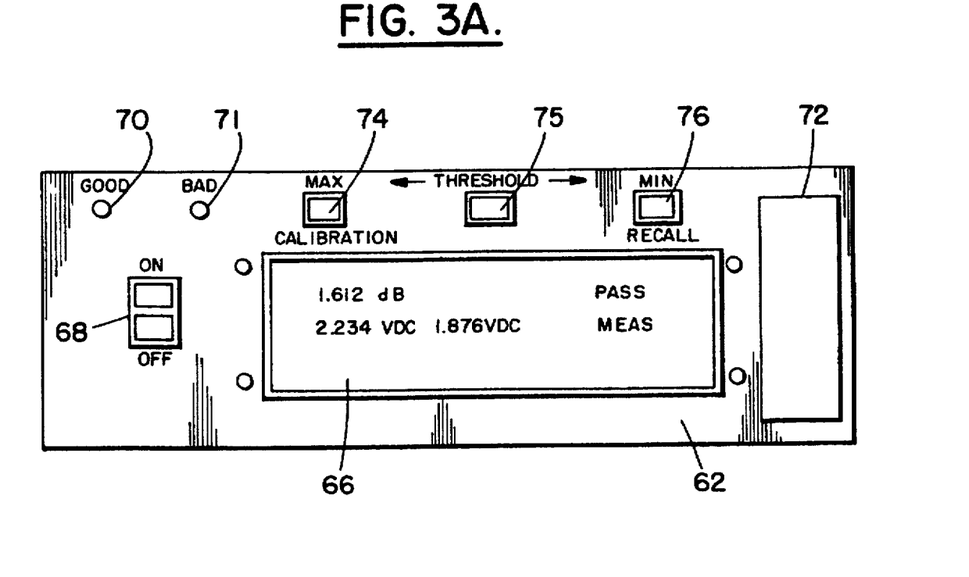
FIG. 3A is an elevational front view of the control and display panel shown in FIG. 3.

Referring now to FIG. 3, there is shown a perspective of a portable system 50 incorporating features of the present invention. In the embodiment shown, the portable system 50 includes a portable scan device 52 and a portable display 54. The portable scan device 52 includes a holder 56, a transceiver 12, and a hand operated plunger 58. The portable hand held scan device 52 is operably connected to the portable display 54 by cable 60. Referring also to FIG. 3A, the portable display 54 has a front control and display panel 62 located at the front of the housing 64. I/O ports (not shown) are located at the back of the housing 64. A digital signal processor 80 is located inside the housing 64. A battery 82 is located in the housing 64 for powering the electronics of the display 54 and the hand held scanner 52. However, suitable means could be provided to electrically connect the system 50 to a standard electrical outlet. The display 54 could also include its own internal recording device and/or electronic memory. Also located in the display is a microprocessor 84 for performing other necessary and/or desired processing. The front panel 62 includes an LCD display 66, an on-off switch 68, two LED's 70, 71, a buzzer 72, and three switches 74, 75, 76. The cable 60 is connected to one of the I/O ports (not shown) at the back of the housing 64. Another cable 78 is shown in FIG. 3 which is connected to another I/O port (not shown) at the back of the housing 64. The cable 78 can be connected to a suitable device such as a computer or recording log device. In a preferred embodiment, a cable mounted log button (not shown) is connected to the portable display 54 to be used to log in peak signals of measurements.

Figure 4:
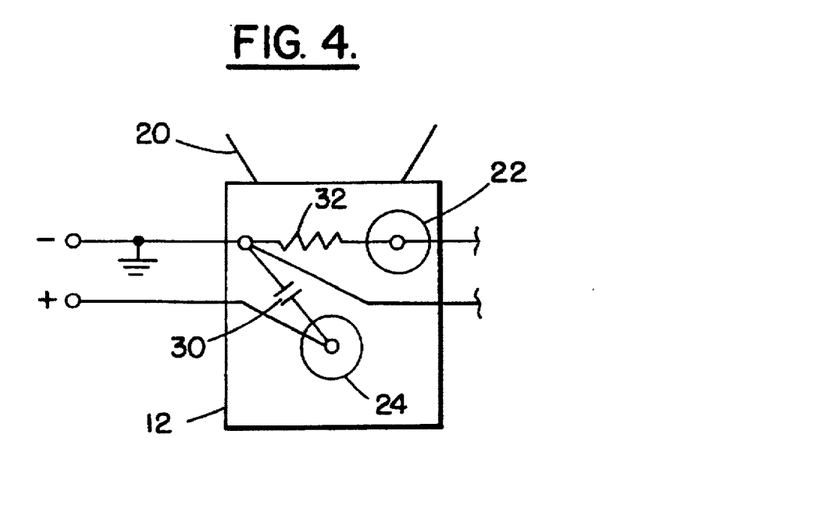
FIG. 4 is a schematic diagram of a transceiver used in the system shown in FIG. 3.

Referring also to FIG. 4, a schematic diagram of the transceiver 12 is shown. The transceiver 12 is essentially the same type of transceiver described with reference to FIG. 1 above. The transceiver 12 includes the horn antenna 20, the mixer 22, the oscillator 24, the capacitor 30, and the load resistor 32.

Figure 5:
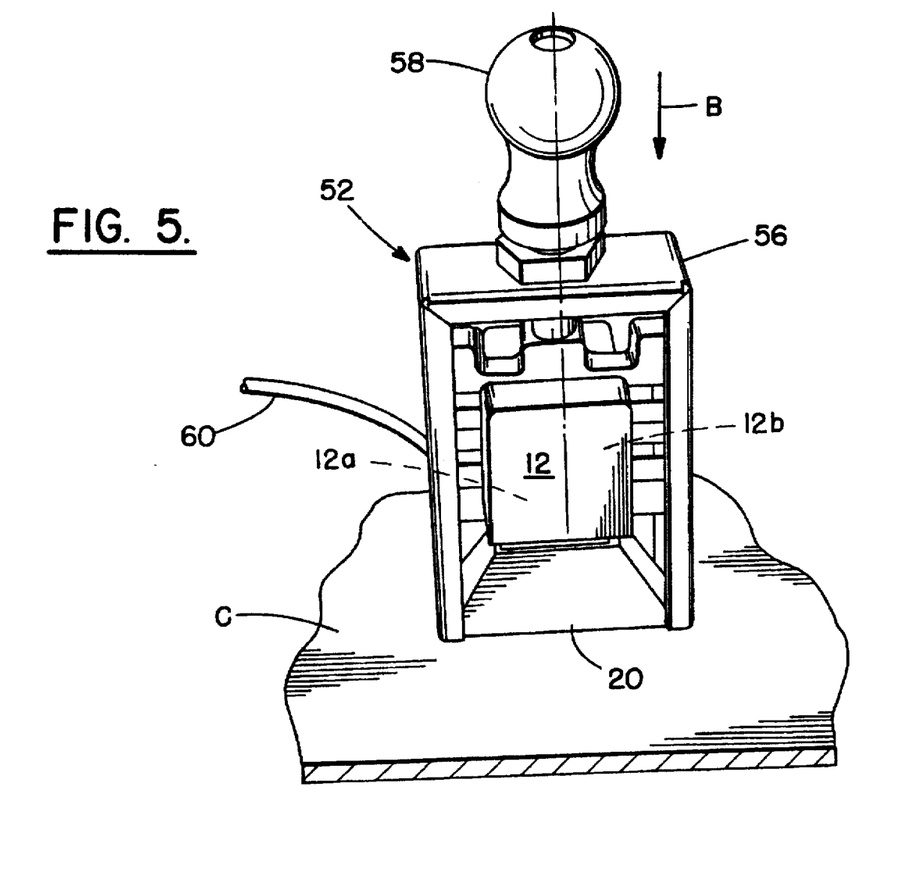
FIG. 5 is a perspective view of the portable scan device shown in FIG. 3 with the transceiver in a down position.

Referring also to FIG. 5, a perspective view of the portable scan device 52 is shown on a member C. The holder 56, in the embodiment shown, functions as a frame for the transceiver 12. In addition, the holder 56 functions as a support for locating the hand held scanner 52 on the surface of the member C. In an alternate embodiment of the invention, any suitable type of holder or frame could be provided, such as a surface traversing vehicle. The transceiver 12 is movably mounted to the holder 56 for movement between up and down positions. FIG. 3 shows the transceiver 12 in an up position. FIG. 5 shows the transceiver 12 in a down position. The hand operated plunger 58 is connected to the transceiver 12. The plunger 58 is preferably biased by a spring (not shown) in the up position. When a user moves the plunger 58 from the up position shown in FIG. 3 to the down position shown in FIG. 5 as indicated in arrow B in FIG. 5, the transceiver 12 is moved from its up position to its down position. When the user releases the plunger 58 the spring (not shown) will bias the plunger 58 back to its up position. The transceiver 12 will thus also return to its up position. In this fashion the transceiver 12 can be moved up and down in the holder 56. With the holder 56 located on the surface of the member C, the transceiver 12 can thus be moved up and down relative to the member C. In alternate embodiments, any suitable type of means can be used to movably mount the transceiver 12 in the holder 56. In addition, a mechanized or automated movement mechanism could be provided to move the transceiver 12 on the holder 56.

The portable system 50 is provided for measuring and recording electromagnetic radiation absorption of magnetically susceptible or electrically conductive surfaces with a battery operated device. The hand held scanner 52 can be positioned on a surface and the transceiver 12 moved up and down above the surface in order to scan for the in phase peak output signal. The output signal from the transceiver 12 is sent to the portable display 54 via the cable 60 as a voltage. The peak voltage is detected and retained by the microprocessor 84. The portable display 54 converts the peak voltage into decibel absorption units which are displayed on the LCD display 66 and can be recorded. The user may press the cable mounted log button (not shown) to record the peak output voltage for that location on the member C. The output can also be converted to resistivity as ohms per square area or coating thickness. The portable system 50 is designed to provide direct real time measurements of specific absorption characteristics. Although the system 50 can be used in production processes to control application of magnetic and resistive low observable coatings, its portability is particularly adapted for field use to assure electrical smoothness of low observable coating and gap repairs. The system 50 may be calibrated to measure conductive paint coat thickness and other parameters such as residual solvent. The system 50 can be used in the field to identify a location on a surface that needs to be repaired. The system 50 can also be used in the field after a repair is made or during repair to measure for and correct to a predetermined desired low observable performance.

Figure 8:
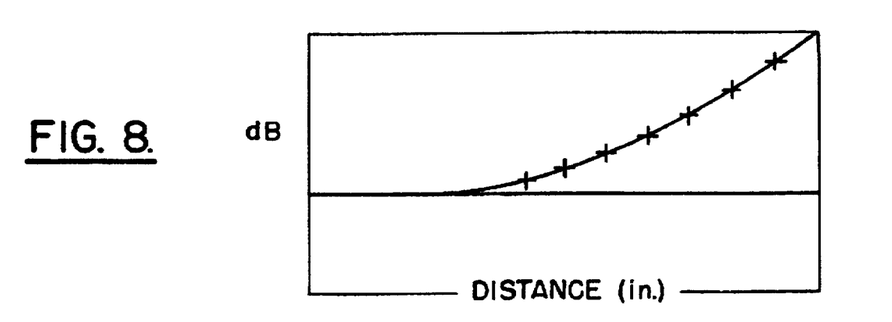
FIG. 8 is a graph of electromagnetic energy reflections in decibels of a surface taper.
Figure 9:
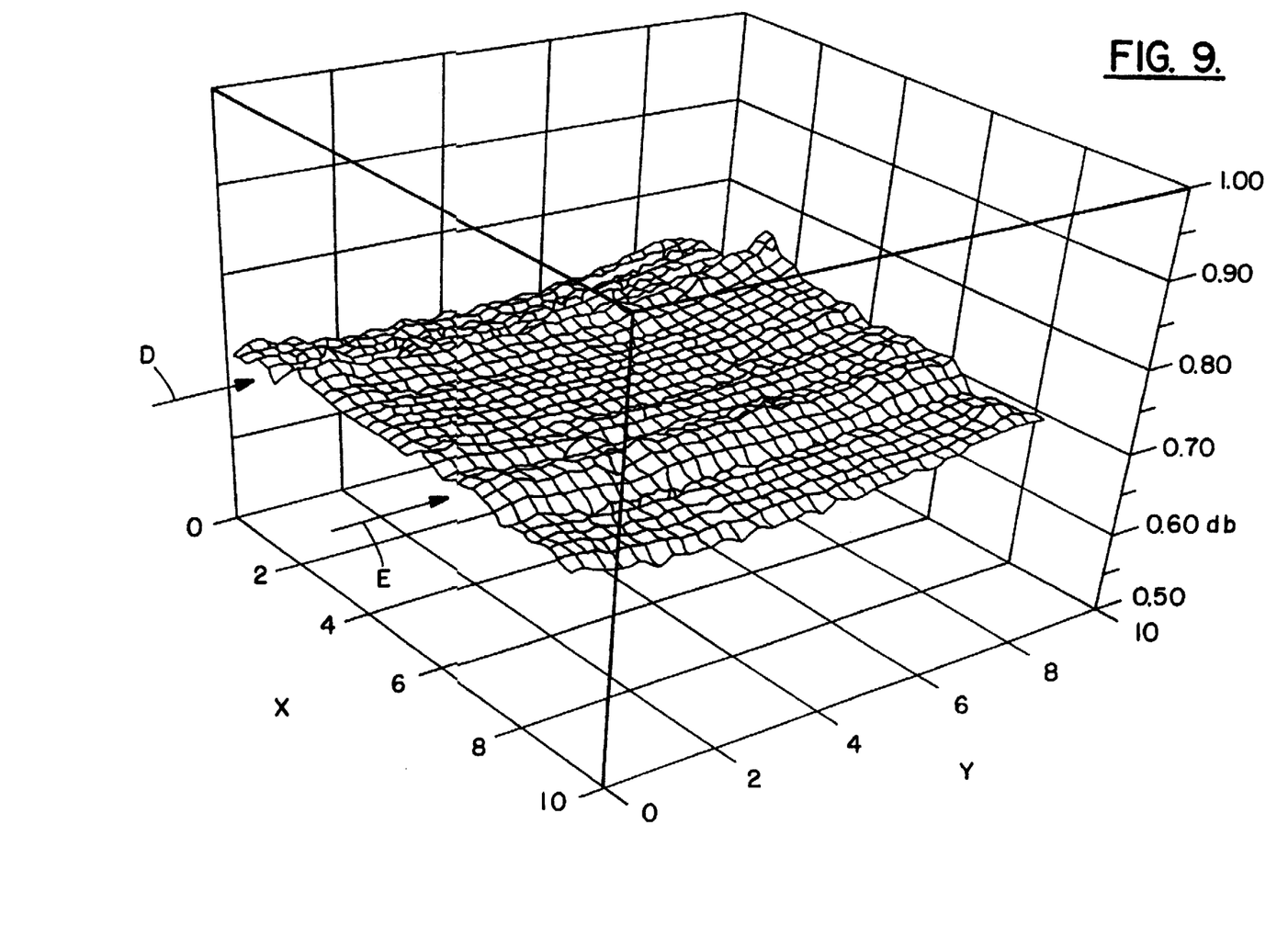
FIG. 9 is a three-dimensional graph of electromagnetic energy reflections in decibels of a surface of a member being tested.

As the transceiver 12 is moved up and down perpendicularly through the interference peaks and valleys of the transmitted and reflected electromagnetic waves, in and out of phase, the varying voltage output from the transceiver 12 is displayed on the LCD display 66. Although the holder 56 has been described as a manually actuated, spring loaded, point to point single peak detection device, the holder could be part of a robotic manipulator or a coordinate measuring machine with a peak detecting proportional control feedback subroutine to maintain the transceiver in phase and generate a peak output voltage at all times as it traverses above a surface. Although the manual scanner 52 can be used to log multiple data points, continuous or overlapping moving average three axis measurements can be made with a robotic or coordinate measuring machine. Plots of electrical topography of low observable and conductive surfaces can be made such as shown in FIG. 9. Detailed graphs of hitherto unavailable low observability tapers can also be provided as illustrated in FIG. 8.

Figure 6:
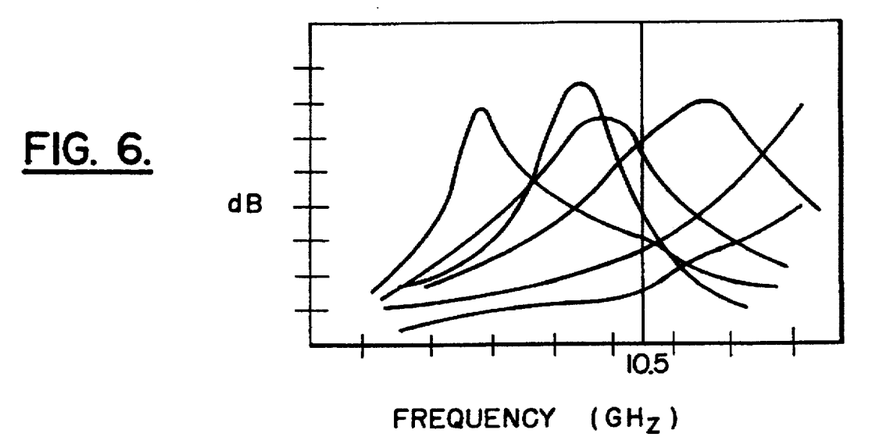
FIG. 6 is a graph of characteristic curves of electromagnetic energy reflections in decibels of different materials at various frequencies.

Referring also to FIG. 6, there is shown a graph of characteristic curves of electromagnetic energy reflections in decibels at different frequencies for various different materials. The transceiver 12 broadcasts at about 10.5 GHz which is in the middle of the X-band radar spectrum. The present invention uses the information from these characteristic curves and the about 10.5 GHz frequency as a snap-shot slice of what reflection should be for a member being tested. Use of this method has been found to be about 98–99% accurate. In alternate embodiments, multiple different transceivers with different broadcast frequencies could be used together. As illustrated by the dashed line in FIG. 5, such transceivers could include C-band (4–8 GHz) transceiver 129 and K-band (24 GHz) transceiver 12b to draw more accurate inferences about low observable performance at intermediate frequencies.

Figure 7:
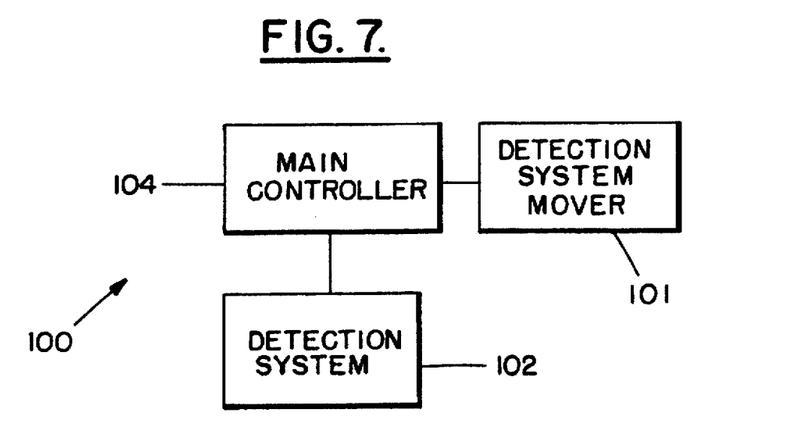
FIG. 7 is a schematic block diagram of an alternate embodiment of a system incorporating features of the present invention.

Referring also to FIG. 7, in a continuous measuring system 100, such as with a robotic or coordinate movement machine 101, deviations from a continuous peak output can be used for process control purposes. The machine 101 is preferably a computer controlled movement mechanism that moves the detection system 102 relative to the member being tested. The output voltages from the transceiver of the detection system 102 for different X-Y coordinates on a surface being tested are fed into an analog-to-digital converter in the main controller 104, and converted to digital data. The firmware residing in the main controller 104 selects the peak voltage and converts it to various units such as decibels, inches or ohms per square area using the following algorithm:

$$Y(\text{decibels}) = A * X(\text{transceiver volts})^B.$$

Coefficients A and B are derived by correlating transceiver output voltages from surfaces with known decibel absorption ratings with the known decibel ratings. Curve fitting equations of, for example, logarithmic and polynomial form may also be derived from the correlation data. The portable system 50 of FIG. 3 is also used to measure the normalized peak voltages from materials which have been otherwise characterized for electromagnetic energy absorption in various units at about 10.5 GHz. This data is used to generate the coefficients of curve fitting equations of, for example, logarithmic or polynomial form to convert the normalized reflected electromagnetic energy in volts to other units such as absorption in decibels, thickness in inches or sheet resistance in ohms per square area. An appropriate conversion equation is inserted into the microprocessor 84 and, thereafter, the peak output voltage of the transceiver and the derived characteristic value, such as absorption in decibels, are displayed on the LCD display 66 and retained in the memory of the portable display 54.

The transceiver output voltage to the analog-to-digital converter is normalized prior to the power equation on a highly reflective material such as steel or aluminum surface so the peak electromagnetic wave energy can be detected and normalized. Normalization of reflected electromagnetic energy for a particular transceiver at a single frequency of about 10.5 GHz is accomplished by moving the transceiver up and down above the highly reflective aluminum or steel surface to scan the in-phase and out-of-phase output voltage for that particular transceiver. This peak output voltage is used by the microprocessor to generate a calibration factor or normalization factor which it thereafter uses to normalize the output voltage of that transceiver. The calibration factor is the quotient of an arbitrary standard peak reflected output of about 2.4 volts divided by the peak reflected output voltage of the transceiver being normalized. The calibration factor is stored and applied to transceiver output voltages to compensate for continuous wave transmitted power variations from one transceiver to another, or the same transceiver over time. prior to making any measurements, a reference coupon can be placed on top of an aluminum or steel plate to set up the maximum reflected energy threshold level (minimum absorption). Any reflected energy higher than this level will initiate an audible alarm from the buzzer 72. In alternate embodiments, other types of operator interface devices could be used.

Measuring and plotting of low observability tapers and three dimensional contour maps of surface electrical topography can provide a new level of refinement and statistical control of low observability coatings to provide and maintain a reduced radar signature. As seen with reference to FIG. 9, a three dimensional contour map of electromagnetic reflectance of a surface can be plotted in decibels based upon values of the transceiver output signal at several locations on a member. Two axes are plotted as X-Y coordinates of the surface and one axis is based upon the values of the output signal. Repair sites D and E can be checked to insure that their reflectance is within tolerable or predetermined levels. If not, the sites D and/or E can be reworked.

It should be understood that the foregoing description is only illustrative of the invention. Various alternatives and modifications can be devised by those skilled in the art without departing from the spirit of the invention. Accordingly, the present invention is intended to embrace all such alternatives, modifications and variances which fall within the scope of the appended claims.

What is claimed is:

1. A method of testing an electromagnetic property of a member comprising steps of:

moving a transceiver towards and away from a portion of the member, the transceiver both transmitting electromagnetic energy towards the portion and receiving reflected electromagnetic energy from the portion as the transceiver is moved toward and away from the portion; and generating an output signal from the transceiver representative of received reflected electromagnetic energy from the portion as the transceiver is moved towards and away from the portion, wherein the transceiver is movably mounted in a holder and the step of moving comprises positioning the holder on the member and moving the transceiver on the holder.

2. A method as in claim 1 wherein the electromagnetic energy is microwave energy.

3. A method as in claim 2 wherein the electromagnetic energy is transmitted from the transceiver at a frequency of about 10.5 GHz.

4. A method as in claim 1 further comprising comparing the received reflected electromagnetic energy to a characteristic curve of reflections for material of which the member is composed.

5. A method as in claim 1 further comprising plotting a graph of the electromagnetic property based upon values of the output signal of the transceiver at several locations of the member.

6. A method as in claim 5 wherein the step of plotting plots a three-dimensional graph with two axes as coordinates of a surface of the member and one axis being based upon the values of the output signal.

7. A method as in claim 5 wherein the values of the output signal are in volts that are converted to decibels.

8. A method as in claim 1 wherein the step of moving comprises a computer controlled movement mechanism that moves the transceiver.

9. A system for measuring an electromagnetic property of a member, the system comprising:

a portable scan device having an electromagnetic energy transceiver and an antenna connected to the transceiver for transmitting electromagnetic energy from the transceiver and for receiving reflected electromagnetic energy; and a portable display operably connected to the scan device, wherein the scan device has a holder with the transceiver movably mounted on the holder and the scan device includes a mechanism for moving the transceiver relative to the holder.

10. A system as in claim 9 wherein the scan device has a holder with the transceiver movably mounted on the holder.

11. A system as in claim 10 wherein the scan device includes a hand operated plunger for moving the transceiver relative to the holder.

12. A system as in claim 9 wherein the mechanism comprises a hand operated plunger.

13. A system as in claim 9 wherein the transceiver includes an electromagnetic energy transmitting diode that transmits at a frequency of about 10.5 GHz.

14. A system as in claim 12 wherein the plunger is spring biased in a predetermined position on the holder.

15. A method as in claim 4 wherein the transceiver broadcasts at a frequency of about 10.5 $GH_z$ and the step of comparing compares the received reflected electromagnetic energy relative to the characteristic curve for the material at 10.5 $GH_z$.

16. A method as in claim 1 wherein the step of moving comprises moving multiple transceivers towards and away from the portion.

17. A method as in claim 16 wherein the multiple transceivers include multiple different transceivers with different broadcast frequencies.

18. A system as in claim 9 wherein the mechanism comprises a computer controlled movement mechanism.

19. A system for measuring an electromagnetic property of a member, the system comprising:

a portable scan device having an electromagnetic energy transceiver, wherein the scan device has a holder with the transceiver movably mounted on the holder and the scan device includes a hand operated plunger for moving the transceiver relative to the holder; and a portable display operably connected to the scan device.

20. A method of testing an electromagnetic property of a member comprising steps of:

moving a transceiver towards and away from a portion of the member, the transceiver both transmitting electromagnetic energy towards the portion and receiving reflected electromagnetic energy from the portion as the transceiver is moved; and generating an output signal from the transceiver representative of received reflected electromagnetic energy, wherein the transceiver is movably mounted in a holder and the step of moving comprises positioning the holder on the member and moving the transceiver on the holder.

* * * * *